United States Patent [19]

Kubota et al.

[11] Patent Number: 5,463,086
[45] Date of Patent: Oct. 31, 1995

[54] PROCESS FOR PRODUCING LACTIDES AND PROCESS FOR PURIFYING CRUDE LACTIDES

[75] Inventors: Kazuomi Kubota; Yoichi Murakami, both of Chiba, Japan

[73] Assignee: Dainippon Ink and Chemicals, Inc., Tokyo, Japan

[21] Appl. No.: 207,197

[22] Filed: Mar. 8, 1994

[30] Foreign Application Priority Data

Mar. 24, 1993 [JP] Japan ................................. 5-65201
Mar. 31, 1993 [JP] Japan ................................. 5-73466

[51] Int. Cl.⁶ .................................................. C07D 319/00
[52] U.S. Cl. .................................................. 549/274
[58] Field of Search ....................................... 549/274

[56] References Cited

U.S. PATENT DOCUMENTS

| | | | |
|---|---|---|---|
| 4,810,775 | 3/1989 | Bendix et al. | 528/480 |
| 4,966,982 | 10/1990 | Ono et al. | 549/274 |
| 4,990,222 | 2/1991 | Aigner et al. | 549/274 |
| 5,043,458 | 8/1991 | Bhatin | 549/274 |
| 5,053,522 | 10/1991 | Muller et al. | 549/274 |
| 5,214,159 | 5/1993 | Muller et al. | 549/274 |
| 5,264,592 | 11/1993 | Friedman et al. | 549/274 |
| 5,319,107 | 6/1994 | Benecki et al. | 549/274 |

OTHER PUBLICATIONS

Agnew. Chem. Int. Ed. Engl. 18 (1979), No. 4, pp. 310–311.

*Primary Examiner*—C. Warren Ivy
*Assistant Examiner*—A. A. Owens
*Attorney, Agent, or Firm*—Armstrong, Westerman, Hattori, McLeland & Naughton

[57] ABSTRACT

A process for producing a meso-compound-containing lactide, comprising thermally decomposing a hydroxycarboxylic acid oligomer in the presence of a salt of an alkali metal except sodium and in the presence or absence of a metal of the groups 4 to 15 of the periodic table and/or a salt thereof; and a process for purifying a crude lactide comprising recrystallizing a crude lactide using a poor solvent and a good solvent selected from aliphatic tertiary alcohols, ketones and esters are disclosed. The production ratio of a meso-lactide can be controlled by selection of the kind and the amount of a catalyst so as to obtain a lactide having an appropriate optical purity suitable for production of biodegradable polymers. The purification process achieves a high recovery.

5 Claims, No Drawings

5,463,086

PROCESS FOR PRODUCING LACTIDES AND PROCESS FOR PURIFYING CRUDE LACTIDES

FIELD OF THE INVENTION

This invention relates to a process for producing meso-compound-containing lactides which are useful as a material for biodegradable polymers and a process for purifying the resulting lactide.

BACKGROUND OF THE INVENTION

In recent years, lactides which are dimeric cyclic esters obtained by thermally decomposing an oligomer of a hydroxycarboxylic acid, e.g., lactic acid, have been attracting attention as a material for biodegradable polymers.

A number of reports have hitherto been made with reference to production of lactides by thermal decomposition of hydroxycarboxylic acid oligomers. For example, German Patent 1083275 discloses a process using a metal of the group IV, V or VIII of the periodic table or a compound thereof (group 4, 5, 8, 9, 10, 14 or 15 according to the latest notation) as a catalyst; German Patent 3708915 describes a process using tin or a tin compound as a catalyst; German Patent 1234703 suggests use of a titanium tetraalkoxide catalyst; and German Patent 250413 teaches use of a zinc oxide catalyst.

Every known process makes it a chief aim to obtain a lactide having a high optical purity. However, polymers prepared from an optically active lactide having a high optical purity exhibit limited characteristics because of the high crystallinity and lack in softness demanded for use as general-purpose polymers as recently expected.

In order to control crystallinity of the lactide polymers, such a troublesome means as mixing a highly optically active lactide with another separately synthesized optically active lactide or an optically inactive lactide has been taken. In other words, the known processes for producing lactides of high optical purity are not always deemed advantageous for production of biodegradable polymers with broader latitude in physical properties to which the latest attention is being directed. It has thus been demanded to develop a process for producing lactides having arbitrary optical purity.

On the other hand, since a crude lactide resulting from thermal decomposition of a hydroxycarboxylic acid oligomer contains impurities, such as lactic acid, and is unsuitable as a starting material for polymers, it should be purified by recrystallization and the like. For example, recrystallization from a diethyl ether/petroleum ether mixed solvent or a substituted benzene solvent (e.g., toluene) is reported in Angew. Chem., Int. Ed. Engl., Vol. 18, p. 310 (1979) or British Patent 1122229, respectively.

Further, Japanese Patent Publication (examined) No. 6673/76 discloses a purifying process comprising adding a molten crude lactide to t-amyl alcohol or t-butyl alcohol at 30° to 50° C. to prepare a slurry having excellent storage stability and further adding the same alcohol to the slurry to conduct recrystallization.

However, any of the conventional purifying processes attains a recovery as low as about 70% and are not regarded industrially advantageous.

SUMMARY OF THE INVENTION

An object of the present invention is to provide a process for producing a meso-compound-containing lactide having an arbitrarily controlled optical purity.

Another object of the present invention is to provide a process for purifying a lactide at a high recovery.

As a result of extensive investigations, the present inventors have found that thermal decomposition of a hydroxycarboxylic acid oligomer in the presence of a salt of an alkali metal except sodium, particularly an alkali metal carbonate as a catalyst results in production of an optically inactive meso-lactide as well as an optically active lactide thereby making it possible to arbitrarily select an optical purity of the product. They have also found that a crude lactide can be purified by recrystallization using a poor solvent and a specific good solvent to provide a purified lactide at a high recovery. The present invention has been completed based on these findings.

The present invention relates to a process for producing a meso-compound-containing lactide, comprising thermally decomposing a hydroxycarboxylic acid oligomer in the presence of a salt of an alkali metal except sodium.

The present invention also relates to a process for purifying a crude lactide, comprising recrystallizing a crude lactide using (A) a poor solvent in which said lactide has a solubility of not more than 1% by weight at 23° C. and (B) a good solvent in which said lactide has a solubility of not Less than 5% by weight at 23° C.

DETAILED DESCRIPTION OF THE INVENTION

The alkali metal salts except a sodium salt which can be used as a catalyst in the present invention preferably include lithium salts and potassium salts.

Specific examples of lithium salts are salts with organic or inorganic salts, e.g., lithium carbonate, lithium chloride, lithium bromide, lithium iodide, lithium hydroxide, lithium sulfate, lithium nitrate, lithium phosphate, lithium acetate, lithium propionate, lithium butyrate, lithium isobutyrate, lithium valerate, lithium isovalerate, lithium caproate, lithium enanthate, lithium caprylate, lithium octanoate (also termed lithium 2-ethylhexanoate), lithium laurate, lithium palmitate, lithium stearate, lithium oleate, lithium oxalate, lithium malonate, lithium succinate, lithium glutarate, lithium adipate, lithium pimelate, lithium suberate, lithium azelate, lithium sebacate, lithium benzoate, lithium α-naphthoate, lithium β-naphthoate, lithium glycolate, lithium lactate, lithium tartrate, lithium mandelate, lithium benzilate, and lithium salicylate.

Specific examples of potassium salts include salts with organic or inorganic acids, e.g., potassium carbonate, potassium hydrogencarbonate, potassium chloride, potassium bromide, potassium iodide, potassium hydroxide, potassium sulfate, potassium nitrate, potassium phosphate, potassium acetate, potassium propionate, potassium butyrate, potassium isobutyrate, potassium valerate, potassium isovalerate, potassium caproate, potassium enanthate, potassium caprylate, potassium octanoate (also termed potassium 2-ethylhexanoate), potassium laurate, potassium palmitate, potassium stearate, potassium oleate, potassium oxalate, potassium malonate, potassium succinate, potassium glutarate, potassium adipate, potassium pimelate, potassium suberate, potassium azelate, potassium sebacate, potassium benzoate, potassium α-naphthoate, potassium β-naphthoate, potassium glycolate, potassium lactate, potassium tartrate, sodium potassium tartrate, potassium mandelate, potassium benzilate, and potassium salicylate. All hydrates and all optical and steric isomers of these salts, if any, are included in the scope of the present invention. Of these salts, carbonates and hydrogencarbonates are particularly preferred because they give off only non-corrosive carbonic acid gas on reacting with a hydroxycarboxylic acid oligomer in the presence of a catalyst.

As previously stated, metals of the groups 4 to 15 of the periodic table and/or salts thereof have often been employed as a catalyst for thermal decomposition of hydroxycarboxylic acid oligomers. In these cases, the production amount of a meso-compound is very small.

It has now been ascertained that use of an alkali metal salt except a sodium salt in combination with a metal of the groups 4 to 15 and/or a salt thereof, preferably a metal of the groups 12 to 15 and/or a salt thereof, as a catalyst makes it possible to change the production ratio of a meso-compound and that the optical purity of the resulting lactide can easily be controlled by changing the production ratio of a meso-compound.

While the metals of the groups 4 to 15 and salts thereof which can be used in the present invention are not particularly limited, those belonging to the groups 12 to 15 and their salts are preferred. Preferred metals of the groups 12 to 15 are zinc, cadmium, aluminum, tin, lead, and antimony. Salts of these metals include zinc salts with organic or inorganic acids, such as zinc carbonate, zinc chloride, zinc bromide, zinc iodide, zinc hydroxide, zinc oxide, zinc sulfide, zinc sulfate, zinc nitrate, zinc phosphate, zinc acetate, zinc propionate, zinc butyrate, zinc isobutyrate, zinc valerate, zinc isovalerate, zinc caproate, zinc enanthate, zinc caprylate, zinc octanoate (or zinc 2-ethylhexanoate), zinc laurate, zinc palmirate, zinc stearate, zinc oleate, zinc oxalate, zinc malonate, zinc succinate, zinc glutarate, zinc adipate, zinc pimelate, zinc suberate, zinc azelate, zinc sebacate, zinc benzoate, zinc α-naphthoate, zinc β-naphthoate, zinc glycolate, zinc lactate, zinc tartrate, zinc mandelate, zinc benzilate, and zinc salicylate; cadmium salts with organic or inorganic acids, such as cadmium carbonate, cadmium chloride, cadmium bromide, cadmium iodide, cadmium hydroxide, cadmium oxide, cadmium sulfide, cadmium sulfate, cadmium nitrate, cadmium phosphate, cadmium acetate, cadmium propionate, cadmium butyrate, cadmium isobutyrate, cadmium valerate, cadmium isovalerate, cadmium caproate, cadmium enanthate, cadmium caprylate, cadmium octanoate (or cadmium 2-ethylhexanoate), cadmium laurate, cadmium palmirate, cadmium stearate, cadmium oleate, cadmium oxalate, cadmium malonate, cadmium succinate, cadmium glutarate, cadmium adipate, cadmium pimelate, cadmium suberate, cadmium azelate, cadmium sebacate, cadmium benzoate, cadmium α-naphthoate, cadmium β-naphthoate, cadmium glycolate, cadmium lactate, cadmium tartrate, cadmium mandelate, cadmium benzilate, and cadmium salicylate; aluminum salts with organic or inorganic acids, e.g., aluminum carbonate, aluminum chloride, aluminum bromide, aluminum iodide, aluminum hydroxide, aluminum oxide, aluminum sulfide, aluminum sulfate, aluminum nitrate, aluminum phosphate, aluminum acetate, aluminum propionate, aluminum butyrate, aluminum isobutyrate, aluminum valerate, aluminum isovalerate, aluminum caproate, aluminum enanthate, aluminum caprylate, aluminum octanoate (or aluminum 2-ethylhexanoate), aluminum laurate, aluminum palmitate, aluminum stearate, aluminum oleate, aluminum oxalate, aluminum malonate, aluminum succinate, aluminum glutarate, aluminum adipate, aluminum pimelate, aluminum suberate, aluminum azelate, aluminum sebacate, aluminum benzoate, aluminum α-naphthoate, aluminum β-naphthoate, aluminum glycolate, aluminum lactate, aluminum tartrate, aluminum mandelate, aluminum benzilate, and aluminum salicylate; tin salts with organic or inorganic acids, e.g., tin carbonate, tin chloride, tin bromide, tin iodide, tin hydroxide, tin oxide, tin sulfide, tin sulfate, tin nitrate, tin phosphate, tin acetate, tin propionate, tin butyrate, tin isobutyrate, tin valerate, tin isovalerate, tin caproate, tin enanthate, tin caprylate, tin octanoate (or tin 2-ethylhexanoate), tin laurate, tin palmirate, tin stearate, tin oleate, tin oxalate, tin malonate, tin succinate, tin glutarate, tin adipate, tin pimelate, tin suberate, tin azelate, tin sebacate, tin benzoate, tin α-naphthoate, tin β-naphthoate, tin glycolate, tin lactate, tin tartrate, tin mandelate, tin benzilate, tin salicylate, dibutyltin oxide, dibutyltin dilaurate, tributyltin chloride, dibutyltin dichloride, tin methoxide, tin ethoxide, tin propoxide, tin isopropoxide, tin butoxide, tin isobutoxide, tin secbutoxide, and tin t-butoxide; lead salts with organic or inorganic acids, e.g., lead carbonate, lead chloride, lead bromide, lead iodide, lead hydroxide, lead oxide, lead sulfide, lead sulfate, lead nitrate, lead phosphate, lead acetate, lead propionate, lead butyrate, lead isobutyrate, lead valerate, lead isovalerate, lead caproate, lead enanthate, lead caprylate, lead octanoate (or lead 2-ethylhexanoate), lead laurate, lead palmitate, lead stearate, lead oleate, lead oxalate, lead malonate, lead succinate, lead glutarate, lead adipate, lead pimelate, lead suberate, lead azelate, lead sebacate, lead benzoate, lead α-naphthoate, lead β-naphthoate, lead glycolate, lead lactate, lead tartrate, lead mandelate, lead benzilate, and lead salicylate; and antimony salts with organic or inorganic acids, e.g., antimony carbonate, antimony chloride, antimony bromide, antimony iodide, antimony hydroxide, antimony oxide, antimony sulfide, antimony sulfate, antimony nitrate, antimony phosphate, antimony acetate, antimony propionate, antimony butyrate, antimony isobutyrate, antimony valerate, antimony isovalerate, antimony caproate, antimony enanthate, antimony caprylate, antimony octanoate (or antimony 2-ethylhexanoate), antimony laurate, antimony palmitate, antimony stearate, antimony oleate, antimony oxalate, antimony malonate, antimony succinate, antimony glutarate, antimony adipate, antimony pimelate, antimony suberate, antimony azelate, antimony sebacate, antimony benzoate, antimony α-naphthoate, antimony β-naphthoate, antimony glycolate, antimony lactate, antimony tartrate, antimony mandelate, antimony benzilate, and antimony salicylate. Every hydrate and every optical or steric isomer, if any, of these salts are included in the scope of the present invention. Further, all the possible salts of those metals having two or more valencies are also included.

The metals of the groups 4 to 11 and/or salts thereof include titanium tetraisopropoxide, etc.

The hydroxycarboxylic acid oligomers which can be used in the present invention are oligomers comprising a hydroxycarboxylic acid unit and having a weight-average molecular weight of from 400 to 5000, and preferably from 1500 to 3500. These oligomers can be prepared in a known manner. To take an instance, 90% lactic acid is dehydrated by heating at an autoclave temperature of from 60° to 200° C. under atmospheric pressure or reduced pressure of 100 Torr or more.

The hydroxycarboxylic acids which can be used in the present invention include lactic acid, hydroxybutyric acid, hydroxyvaleric acid, hydroxycaproic acid, and various derivatives of a hydroxycarboxylic acid, such as an alkyl-substituted hydroxycarboxylic acid (e.g., 2-hydroxy-2-methylbutyric acid or 2-hydroxy-2-methylvaleric acid).

The hydroxycarboxylic acid material for obtaining oligomers may contain a copolymerizable component, such as glycolic acid. The oligomer obtained from such a material undergoes thermal decomposition similarly. In this case, slight alterations are preferably added to the reaction conditions, such as temperature and pressure.

The thermal decomposition of the oligomer can be carried out by heating to an autoclave temperature of from 150° to 200° C. under reduced pressure of from 2 to 25 Torr, and preferably from 5 to 15 Torr, as described in German Patents 1083275, 267826, and 3708915.

The catalyst may previously be present in the hydroxycarboxylic acid oligomer or separately added to the hydroxycarboxylic acid oligomer, which makes no difference in results. The reaction system is selected from a continuous system or a batch system according to the production conditions.

The catalyst is used in a total amount ranging from 0.01 to 5 parts by weight, preferably from 0.05 to 2 parts by weight, and more preferably from 0.1 to 1 part by weight, per 100 parts by weight of the hydroxycarboxylic acid oligomer.

Where the alkali metal salt catalyst is used in combination with the metal of the groups 4 to 15 and/or a salt thereof, the latter is preferably used in an amount of from 0.1 to 10 parts by weight, and preferably from 0.5 to 5 parts by weight, per part by weight of the alkali metal salt.

The production ratio of a meso-compound varies depending on the hydroxycarboxylic acid species, the catalyst species, the amount of the catalyst, and the thermal decomposition conditions. In general, a meso-compound is produced in a proportion of from 7 to 40% by weight in using an alkali metal catalyst alone; and from 5 to 30% by weight in using a combination of an alkali metal and the metal of the groups 12 to 15. Accordingly, the production ratio of an optically inactive meso-compound can be controlled in a range of from 4 to 40% by weight by choice of the catalyst.

A preferred optical purity of a lactide for use in production of polymers is subject to variation according to the end use of the polymer. From the standpoint of moldability, it is preferable that an L-lactide or a D-lactide has an optical purity of from 80 to 98% by weight, and such an optical purity can be achieved by using a lactide containing 4 to 40% by weight of a meso-lactide. Where a lactide having a higher meso-lactide content, i.e., a lactide having an optical purity of less than 80% is desired, an optically inactive racemic hydroxycarboxylic acid is added to the starting hydroxycarboxylic acid in an arbitrary proportion.

The process for purifying a crude lactide according to the present invention comprises recrystallizing a crude lactide using (A) a poor solvent and (B) at least one good solvent selected from the group consisting of tertiary alcohols, ketones, and esters. The process may further comprise subjecting the thus obtained recrystallization product to further recrystallization using (C) an aromatic hydrocarbon solvent and (D) an aliphatic hydrocarbon solvent having from 5 to 12 carbon atoms.

The crude lactide which can be purified by the above-mentioned recrystallization includes a crude lactide mainly comprising a lactide and also containing the starting materials, such as lactic acid, either as produced or after being partially purified so as to contain small amounts of the starting material.

While any solvent having low capability of dissolving a crude lactide may serve as poor solvent (A), solvents in which the lactide has a solubility of not more than 1% by weight at 23° C. are preferred. In particular, those having a boiling point of 50° C. or higher are preferred for allowing to make a great difference between heating temperature and cooling temperature thereby making the recrystallizing operation easier.

Specific examples of suitable poor solvent (A) include hydrocarbons, e.g., cyclohexane, methylcyclohexane, hexane, heptane, octane, ligroin, and 2,2,4-trimethylpentane. While these hydrocarbon solvents can be used without any limitation, aliphatic hydrocarbons having from 5 to 12 carbon atoms, especially ligroin, heptane, and 2,2,4-trimethylpentane, are preferred.

While any solvent having high capability of dissolving a crude lactide may serve as good solvent (B), solvents in which the lactide has a solubility of not less than 5% by weight at 23° C. are preferred. In particular, those having a boiling point of 50° C. or higher are preferred for allowing to make a great difference between heating temperature and cooling temperature thereby making the recrystallizing operation easier.

Specific examples of suitable good solvents (B) include aliphatic tertiary alcohols, e.g., t-butyl alcohol and t-amyl alcohol; ketones, e.g., methyl ethyl ketone; and esters, e.g., ethyl acetate, methyl acetate, and methyl propionate.

Among them, aliphatic tertiary alcohols are the most preferred in industry for achieving a high recovery and providing a highly pure recrystallization product through single recrystallizing operation. Particularly preferred are t-amyl alcohol and t-butyl alcohol.

Recrystallization is performed by dissolving a crude lactide under heat in the recrystallizing solvent until the solid content of the crude lactide disappears and then cooling the solution to precipitate crystals. Where a single recrystallizing operation is insufficient, the operation may be repeatedly conducted.

The mode of addition of poor solvent (A) is not restricted as long as poor solvent (A) is present in the recrystallizing system before cooling. That is, poor solvent (A) may previously be mixed with good solvent (B), or a crude lactide is first dissolved in good solvent (B) under heat and then poor solvent (A) is added thereto.

The heating temperature is between a temperature at which the solid content disappears and a boiling temperature of the system, and preferably between 50° and 95° C. The cooling temperature is not higher than room temperature and not lower than the solidification point, and preferably between room temperature and 0° C. at which crystals sufficiently precipitate.

The weight ratio of a crude lactide to the total recrystallizing solvent is not particularly critical and preferably ranges from 1:1 to 1:5. The weight ratio of poor solvent (A) to good solvent (B) is not also critical and preferably ranges from 1:1 to 5:1.

In the case where an aliphatic tertiary alcohol is used as a recrystallizing solvent, the resulting product contains substantially no hydroxycarboxylic acid or an oligomer thereof whether or not it is used in combination with a poor solvent. In this case, however, the product contains the tertiary alcohol not much but in a concentration of 1000 ppm or less. The residual tertiary alcohol is taken into the crystal and cannot be removed simply by washing and drying under reduced pressure. Such a residual alcohol can be removed by further subjecting the crystal to recrystallization using (C) an aromatic hydrocarbon solvent and (D) an aliphatic hydrocarbon solvent having from 5 to 12 carbon atoms.

While any aromatic hydrocarbon can be employed as solvent (C), benzene or derivatives thereof, e.g., toluene, xylene, ethylbenzene and mesitylene, are particularly preferred.

Aliphatic hydrocarbon solvent (D) having 5 to 12 carbon atoms include those having an L-lactide dissolving power of not more than 1% by weight at 23° C. In particular, those having a boiling point of 50° C. or higher are preferred for allowing to make a great difference between heating temperature and cooling temperature thereby making the recrystallizing operation easier. Specific examples of such aliphatic hydrocarbons are petroleum ether, cyclohexane, methylcyclohexane, hexane, heptane, octane, ligroin, and 2,2,4-trimethylpentane, with ligroin, heptane, and 2,2,4-trimethylpentane being particularly preferred.

The weight ratio of a lactide to the total recrystallizing solvent is not particularly critical and preferably ranges from 1:1 to 1:5. The weight ratio of aromatic hydrocarbon (C) to aliphatic hydrocarbon (D) is not also critical and preferably ranges from 4:1 to 1:4.

Where the lactide to be purified has small contents of acidic impurities, such as lactic acid, the recrystallizing solvent may be used repeatedly. This simplifies the operating conditions, reduces the requisite times of solvent recovery, and because the lactide once recrystallized is saturated, virtually eliminate the loss of the product.

The present invention will now be illustrated in greater detail with reference to Examples, but the present invention should not be construed as being limited thereto. All the percents are by weight unless otherwise indicated. Further, the total composition of lactide measured by capillary gas chromatography and high-performance liquid chromatography as shown in the following examples is not always 100% and may represent more than 100%.

EXAMPLE 1

A mixture of 151.5 g of 90% L-lactic acid (reduced to a lactic acid monomer), 0.26 g of tin octanoate, and 0.25 g of lithium carbonate was dehydrated by heating to a reactor temperature of 184° C. over 3 hours under reduced pressure of from 100 to 27.5 Torr. The reaction mixture was distilled at 116° to 132° C. under reduced pressure of 7.5 Torr to obtain 95.2 g of a white lactide.

As a result of capillary gas chromatography (hereinafter abbreviated as CGC) using an optically active column and high-performance liquid chromatography (HPLC) using an ODS (octadecylsilane) column, the resulting lactide was found to have the following composition.

L-Lactide: 62.7%
D-Lactide: 3.5%
Meso-lactide: 13.4%
Lactic acid monomer: 6.8%
Lactic acid dimer: 1.6%
Lactic acid trimer: 0.8%
Lactic acid tetramer: 0.3%

EXAMPLE 2

A mixture of 151.5 g of the same 90% lactic acid as used in Example 1, 0.41 g of tin octanoate, and 0.10 g of lithium carbonate was dehydrated by heating to a reactor temperature of 184° C. over 2.5 hours under reduced pressure of from 100 to 27.5 Torr. The reaction mixture was then distilled under reduced pressure of 7.5 Torr at 130° to 140° C. to obtain 97.2 g of a white lactide.

As a result of CGC and HPLC, the resulting lactide was found to have the following composition.

L-Lactide: 69.2%
D-Lactide: 0.9%
Meso-lactide: 13.1%
Lactic acid monomer: 7.6%
Lactic acid dimer: 1.5%
Lactic acid trimer: 1.0%
Lactic acid tetramer: 0.4%

EXAMPLE 3

A mixture of 151.5 g of the same 90% lactic acid as used in Example 1, 0.25 g of tin octanoate, and 0.25 g of lithium carbonate was dehydrated by heating to a reactor temperature of 192° C. over 3 hours under reduced pressure of from 100 to 27.5 Torr. The reaction mixture was distilled under reduced pressure of 7.5 Torr at 115° to 125° C. to obtain 98.4 g of a white lactide.

As a result of CGC and HPLC, the resulting lactide was found to have the following composition.

L-Lactide: 58.8%
D-Lactide: 6.5%
Meso-lactide: 23.1%
Lactic acid monomer: 6.3%
Lactic acid dimer: 0.5%
Lactic acid trimer: 0.4%

EXAMPLE 4

A mixture of 151.5 g of the same 90% lactic acid as used in Example 1, 0.41 g of tin octanoate, and 0.10 g of lithium carbonate was dehydrated by heating to a reactor temperature of 173° C. over 3 hours under reduced pressure of from 100 to 27.5 Torr. The reaction mixture was distilled under reduced pressure of 7.5 Torr at 125° to 137° C. to obtain 102.4 g of a white lactide.

As a result of CGC and HPLC, the resulting lactide was found to have the following composition.

L-Lactide: 70.6%
D-Lactide: 0.8%
Meso-lactide: 7.8%
Lactic acid monomer: 11.0%
Lactic acid dimer: 3.0%
Lactic acid trimer: 1.4%
Lactic acid tetramer: 0.8%

EXAMPLE 5

A mixture of 151.6 g of the same 90% lactic acid as used in Example 1, 0.25 g of zinc acetate dihydrate, and 0.25 g of lithium carbonate was dehydrated by heating to a reactor temperature of 181° C. over 3 hours under reduced pressure of from 100 to 27.5 Torr. The reaction mixture was distilled under reduced pressure of 7.5 Torr at 115° to 125° C. to obtain 81.4 g of a white lactide.

As a result of CGC and HPLC, the resulting lactide was found to have the following composition.

L-Lactide: 69.7%
D-Lactide: 4.5%
Meso-lactide: 19.9%

Lactic acid monomer: 8.8%

Lactic acid dimer: 0.7%

Lactic acid trimer: 0.5%

EXAMPLE 6

A mixture of 151.5 g of the same 90% lactic acid as used in Example 1, 0.40 g of titanium tetraisopropoxide, and 0.10 g of lithium carbonate was dehydrated by heating to a reactor temperature of 177° C. over 3 hours under reduced pressure of from 100 to 27.5 Torr. The reaction mixture was distilled under reduced pressure of 7.5 Torr at 120° to 132° C. to obtain 72.4 g of a white lactide.

As a result of CGC and HPLC, the resulting lactide was found to have the following composition.

L-Lactide: 60.8%

D-Lactide: 4.1%

Meso-lactide: 4.8%

Lactic acid monomer: 10.0%

Lactic acid dimer: 1.9%

Lactic acid trimer: 0.5%

Lactic acid tetramer: 4.1%

EXAMPLE 7

A mixture of 151.5 g of the same 90% lactic acid as used in Example 1 and 0.50 g of lithium carbonate was dehydrated by heating to a reactor temperature of 173° C. over 3 hours under reduced pressure of from 100 to 27.5 Torr. The reaction mixture was distilled under reduced pressure of 7.5 Torr at 113° to 132° C. to obtain 95.1 g of a white lactide.

As a result of CGC and HPLC, the resulting lactide was found to have the following composition.

L-Lactide: 52.1%

D-Lactide: 5.5%

Meso-lactide: 21.0

Lactic acid monomer: 8.8%

Lactic acid dimer: 0.6%

Lactic acid trimer: 0.1%

Lactic acid tetramer: 0.1%

EXAMPLE 8

A mixture of 151.5 g of the same 90% lactic acid as used in Example 1 was dehydrated by heating to a reactor temperature of 165° C. over 3 hours under reduced pressure of from 100 to 27.5 Torr. To the resulting lactic acid oligomer was added 0.50 g of lithium carbonate, and the mixture was distilled under reduced pressure of 7.5 Torr at 115° to 135° C. to obtain 93.7 g of a white lactide.

As a result of CGC and HPLC, the resulting lactide was found to have the following composition.

L-Lactide: 58.7%

D-Lactide: 1.9%

Meso-lactide: 10.4%

Lactic acid monomer: 13.5%

Lactic acid dimer: 2.8%

Lactic acid trimer: 1.3%

Lactic acid tetramer: 0.3%

EXAMPLE 9

A mixture of 151.5 g of the same 90% lactic acid as used in Example 1 and 0.50 g of potassium carbonate was dehydrated by heating to a reactor temperature of 192° C. over 2.3 hours under reduced pressure of from 100 to 27.5 Torr. The mixture was then distilled under reduced pressure of 7.5 Tort at 120° to 130° C. to obtain 92.3 g of a white lactide.

As a result of CGC and HPLC, the resulting lactide was found to have the following composition.

L-Lactide: 40.0%

D-Lactide: 15.4%

Meso-lactide: 26.6%

Lactic acid monomer: 9.3%

Lactic acid dimer: 1.4%

Lactic acid trimer: 0.2%

COMPARATIVE EXAMPLE 1

A mixture of 151.5 g of the same 90% lactic acid as used in Example 1 and 0.50 g of tin powder was dehydrated by heating to a reactor temperature of 173° C. over 3 hours under reduced pressure of from 100 to 27.5 Torr. The mixture was distilled under reduced pressure of 7.5 Torr at 120° to 125° C. to obtain 101.5 g of a white lactide.

As a result of CGC and HPLC, the resulting lactide was found to have the following composition.

L-Lactide: 88.1%

Meso-lactide: 1.3%

Lactic acid monomer: 4.8%

Lactic acid dimer: 0.8%

Lactic acid trimer: 0.6%

Lactic acid tetramer: 0.1%

It is seen that the selectivity to L-lactide is too high to produce a substantial amount of a meso-lactide.

COMPARATIVE EXAMPLE 2

A mixture of 151.0 g of the same 90% lactic acid as used in Example 1 and 0.50 g of tin octanoate was dehydrated by heating to a reactor temperature of 185° C. over 3 hours under reduced pressure of from 100 to 27.5 Torr. The mixture was distilled under reduced pressure of 7.5 Torr at 122° to 130° C. to obtain 97.3 g of a white lactide.

As a result of CGC and HPLC, the resulting lactide was found to have the following composition.

L-Lactide: 83.9%

Meso-lactide: 1.5%

Lactic acid monomer: 8.0%

Lactic acid dimer: 2.2%

Lactic acid trimer: 0.7%

It is seen that the selectivity to L-lactide is too high to produce a substantial amount of meso-lactide.

COMPARATIVE EXAMPLE 3

A mixture of 151.5 g of the same 90% lactic acid as used in Example 1, 0.26 g of tin octanoate, and 0.25 g of sodium sulfide nonahydrate was dehydrated by heating to a reactor temperature of 190° C. over 2.75 hours under reduced pressure of from 100 to 27.5 Torr. The mixture was then distilled under reduced pressure of 7.5 to 14 Torr at 110° to 128° C. to obtain 73.9 g of a white lactide.

As a result of CGC and HPLC, the resulting lactide was found to have the following composition.

L-Lactide: 62.7%

D-Lactide: 5.7%

Meso-lactide: 18.0%

Lactic acid monomer: 8.9%

Lactic acid dimer: 6.0%

Lactic acid trimer: 1.3%

Lactic acid tetramer: 0.5%

REFERENCE EXAMPLE

The L-lactide dissolving power of solvents used in Examples and Comparative Examples hereinafter described was determined as follows. The results obtained are shown in Table 1 below.

A crude lactide slurry having the following composition, which was prepared by thermal decomposition of a hydroxycarboxylic acid oligomer, was stirred in the solvent shown in Table 1 at 23° C. for about 1 hour, and the supernatant liquor (saturated solution) was analyzed by reverse phase HPLC by means of an ODS column using tartaric acid as an internal standard.

Crude Lactide Composition (HPLC):

L-Lactide: 89.6%

Meso-lactide: 4.0%

Lactic acid monomer: 2.2%

Lactic acid dimer: 0.2

Lactic acid trimer: 0.2%

TABLE 1

L-Lactide Dissolving Power (23° C.)

| Solvent | Solubility of L-Lactide (wt %) |
|---|---|
| t-Butyl alcohol | 5.6 |
| t-Amyl alcohol | 5.6 |
| Methyl ethyl ketone | 38.1 |
| Ethyl acetate | 27.0 |
| Ligroin | 0.1 |
| 2,2,4-Trimethylpentane | 0.1 |
| Diethyl ether | 4.7 |
| Toluene | 7.7 |

EXAMPLE 10

In 50.88 g of a 1:2 (by weight, hereinafter the same) mixed solvent of t-butyl alcohol and heptane was dissolved 20.07 g of a crude lactide at 77° C., followed by cooling to 4° C. The thus precipitated crystal was separated and dried under reduced pressure to obtain 18.18 g of colorless prism crystals at a recovery of 90.6%.

The compositions of the crude lactide and the recrystallized product as analyzed by reverse phase HPLC by means of an ODS column using tartaric acid as an internal standard were as follows.

| | Crude Lactide (%) | Recrystallized Product (%) |
|---|---|---|
| L-Lactide | 85.0 | 96.3 |
| Meso-lactide | 3.5 | 1.0 |
| Lactic acid monomer | 5.4 | 0.1 |
| Lactic acid dimer | 0.7 | 0.0 |
| Lactic acid trimer | 0.5 | 0.0 |

EXAMPLE 11

In 49.84 g of a 1:2 mixed solvent of t-amyl alcohol and 2,2,4-trimethylpentane was dissolved 19.84 g of a crude lactide at 83° C., followed by cooling to 4° C. The thus precipitated crystal was separated and dried under reduced pressure to obtain 18.11 g of colorless needle-like crystals at a recovery of 91.3%.

The compositions of the crude lactide and the recrystallized product as analyzed in the same manner as in Example 10 were as follows.

| | Crude Lactide (%) | Recrystallized Product (%) |
|---|---|---|
| L-Lactide | 85.0 | 98.3 |
| Meso-lactide | 3.5 | 0.7 |
| Lactic acid monomer | 5.4 | 0.1 |
| Lactic acid dimer | 0.7 | 0.0 |
| Lactic acid trimer | 0.5 | 0.1 |

EXAMPLE 12

In 50.13 g of a 1:2 mixed Solvent of t-butyl alcohol and 2,2,4-trimethylpentane was dissolved 20.13 g of a crude lactide at 77° C., followed by cooling to 2° C. The thus precipitated crystal was separated and dried under reduced pressure to obtain 18.21 g of colorless needle-like crystals at a recovery of 90.5%.

The compositions of the crude lactide and the recrystallized product as analyzed in the same manner as in Example 10 were as follows.

| | Crude Lactide (%) | Recrystallized Product (%) |
|---|---|---|
| L-Lactide | 85.0 | 98.7 |
| Meso-lactide | 3.5 | 0.7 |
| Lactic acid monomer | 5.4 | 0.0 |
| Lactic acid dimer | 0.7 | 0.0 |
| Lactic acid trimer | 0.5 | 0.1 |

The t-butyl alcohol content in the recrystallized product was 310 ppm as measured by CGC. The recrystallized product had an acid value of 1.96 mg/g.

EXAMPLE 13

In 30.66 g of a 1:2 mixed solvent of t-butyl alcohol and 2,2,4-trimethylpentane was dissolved 12.26 g of a crude lactide at 78° C., followed by cooling. When the temperature dropped to 69° C., several milligrams of purified L-lactide were added thereto as seed crystals, and cooling was continued to 21° C. The thus precipitated crystal was separated and dried under reduced pressure to obtain 10.55 g of colorless prism crystals at a recovery of 86.1%.

The compositions of the crude lactide and the recrystallized product as analyzed in the same manner as in Example 10 were as follows.

|  | Crude Lactide (%) | Recrystallized Product (%) |
|---|---|---|
| L-Lactide | 88.5 | 96.4 |
| Meso-lactide | 3.5 | 0.7 |
| Lactic acid monomer | 2.2 | 0.0 |
| Lactic acid dimer | 1.1 | 0.0 |
| Lactic acid trimer | 0.3 | 0.0 |

EXAMPLE 14

To 69.2 g of a 1:2 mixed solvent of t-butyl alcohol and 2,2,4-trimethylpentane was added 30.1 g of a crude lactide, and the mixture was heated up to 78° C., followed by cooling to 22° C. The thus precipitated crystal was separated and dried under reduced pressure to obtain 28.0 g of white crystals at a recovery of 93.0%.

The compositions of the crude lactide and the recrystallized product as analyzed in the same manner as in Example 10 were as follows.

|  | Crude Lactide (%) | Recrystallized Product (%) |
|---|---|---|
| DL-Lactide | 4.2 | 3.0 |
| Meso-lactide | 94.4 | 97.0 |
| Lactic acid dimer | 1.4 | 0.0 |

The t-butyl alcohol content remaining in the recrystallized product was found to be 720 ppm as measured by CGC.

To 19.9 g of a 1:0.593 mixed solvent of toluene and 2,2,4-trimethylpentane was added 12.5 g of the resulting recrystallized product, and the mixture was once heated up to 50° C. and then cooled to 24° C. The crystal was separated and dried under reduced pressure to obtain 10.6 g of a white solid at a recovery of 84.8%. t-Butyl alcohol was no more detected by CGC in the resulting recrystallized product.

The composition of the thus purified lactide as analyzed in the same manner as in Example 10 is shown below.

|  | Recrystallized Product (%) |
|---|---|
| DL-Lactide | 2.4 |
| Meso-lactide | 97.6 |

EXAMPLE 15

To 100.89 g of a 1:2 mixed solvent of t-butyl alcohol and 2,2,4-trimethylpentane was added 40.35 g of a crude lactide, and the mixture was heated up to 76° C., followed by cooling to 24° C. The thus precipitated crystal was separated and dried under reduced pressure to obtain 33.89 g of a white solid at a recovery of 84.0%.

The compositions of the crude lactide and the recrystallized product as analyzed in the same manner as in Example 10 were as follows.

|  | Crude Lactide (%) | Recrystallized Product (%) |
|---|---|---|
| L-Lactide | 85.0 | 96.5 |
| Meso-lactide | 4.6 | 0.5 |
| Lactic acid monomer | 5.9 | 0.1 |
| Lactic acid dimer | 1.4 | 0.2 |
| Lactic acid trimer | 0.6 | 0.0 |

The t-butyl alcohol content remaining in the recrystallized product was found to be 310 ppm as measured by CGC.

To 32.02 g of a 1:1 mixed solvent of toluene and 2,2,4-trimethylpentane was added 16.05 g of the resulting recrystallized product, and the mixture was once heated up to 95° C. and then cooled to 24° C. The crystal was separated and dried under reduced pressure to obtain 15.35 g of a white solid at a recovery of 95.6%. t-Butyl alcohol was no more detected by CGC in the resulting recrystallized product.

The composition of the thus purified lactide as analyzed in the same manner as in Example 10 is shown below.

|  | Recrystallized Product (%) |
|---|---|
| L-Lactide | 96.9 |
| Meso-lactide | 0.1 |

EXAMPLE 16

In 31.60 g of a 1:2 mixed solvent of t-butyl alcohol and ligroin was dissolved 12.61 g of a crude lactide at 55° C. and cooled to 18° C. The precipitated crystal was separated and dried under reduced pressure to obtain 10.83 g of a recrystallized product at a recovery of 85.9%.

The compositions of the crude lactide and the recrystallized product as analyzed in the same manner as in Example 10 were as follows.

|  | Crude Lactide (%) | Recrystallized Product (%) |
|---|---|---|
| L-Lactide | 86.7% | 95.9% |
| Meso-lactide | 7.3% | 0.9% |
| Lactic acid monomer | 1.7% | 0.0% |
| Lactic acid dimer | 0.2% | 0.0% |
| Lactic acid trimer | 1.6% | 0.0% |

The t-butyl alcohol content remaining in the recrystallized product was found to be 450 ppm by CGC. The acid value of the recrystallized product was 1.18 mg/g.

EXAMPLE 17

In 25.80 g of a 1:4 mixed solvent of methyl ethyl ketone and ligroin was dissolved 10.27 g of a crude lactide at 79° C. and cooled to 24° C. The precipitated crystal was separated and dried under reduced pressure to obtain 8.01 g of a recrystallized product as a colorless needle-like crystal at a recovery of 78.0%.

The compositions of the crude lactide and the recrystallized product as analyzed in the same manner as in Example 10 were as follows.

|  | Crude Lactide (%) | Recrystallized Product (%) |
|---|---|---|
| L-Lactide | 89.6% | 96.6% |
| Meso-lactide | 4.0% | 1.0% |
| Lactic acid monomer | 2.2% | 0.2% |
| Lactic acid dimer | 0.2% | 0.0% |
| Lactic acid trimer | 0.2% | 0.1% |

EXAMPLE 18

In 25.11 g of a 1:3 mixed solvent of ethyl acetate and 2,2,4-trimethylpentane was dissolved 10.06 g of a crude lactide at 79° C. and cooled to 23° C. The precipitated crystal was separated and dried under reduced pressure to obtain 8.81 g of a recrystallized product as a colorless needle-like crystal at a recovery of 87.6%.

The compositions of the crude lactide and the recrystallized product as analyzed in the same manner as in Example 10 were as follows.

|  | Crude Lactide (%) | Recrystallized Product (%) |
|---|---|---|
| L-Lactide | 89.6% | 96.1% |
| Meso-lactide | 4.0% | 0.9% |
| Lactic acid monomer | 2.2% | 0.5% |
| Lactic acid dimer | 0.2% | 0.2% |
| Lactic acid trimer | 0.2% | 0.3% |

COMPARATIVE EXAMPLE 4

In 41.43 g of diethyl ether was dissolved 2.19 g of a crude lactide at 34° C., and 6.80 g of petroleum ether having a boiling point of 30° to 60° C. was added to the solution. After cooling to 20° C., the precipitated crystal was separated and dried under reduced pressure to recover 1.09 g of a recrystallized product (designated product 1). The mother liquor was concentrated under reduced pressure to about a half volume, and the thus precipitated crystal was separated and dried under reduced pressure to recover 0.44 g of a recrystallized product (designated product 2). The total recovery of products 1 and 2 was 69.9%. The compositions of the crude lactide, product 1, and product 2 as analyzed in the same manner as in Example 10 were as follows.

|  | Crude Lactide (%) | Product 1 (%) | Product 2 (%) |
|---|---|---|---|
| L-Lactide | 89.6 | 97.3 | 98.6 |
| Meso-lactide | 4.0 | 0.5 | 1.2 |
| Lactic acid monomer | 2.2 | 0.0 | 0.0 |
| Lactic acid dimer | 0.2 | 0.0 | 0.0 |
| Lactic acid trimer | 0.2 | 0.0 | 0.1 |

COMPARATIVE EXAMPLE 5

In 20.70 g of toluene was dissolved 11.32 g of a crude lactide at 55° C., and the solution was cooled to 18° C. The crystal was separated and dried under reduced pressure only to recover 8.32 g (74.2%) of a recrystallized product. The compositions of the crude lactide and the recrystallized product as analyzed in the same manner as in Example 10 were as follows.

|  | Crude Lactide (%) | Recrystallized Product (%) |
|---|---|---|
| L-Lactide | 86.7% | 97.4% |
| Meso-lactide | 7.3% | 1.4% |
| Lactic acid monomer | 1.7% | 0.2% |
| Lactic acid dimer | 0.2% | 0.0% |
| Lactic acid trimer | 1.6% | 0.1% |

COMPARATIVE EXAMPLE 6

In 30.06 g of t-amyl alcohol was dissolved 15.08 g of a crude lactide at 66° C., and the solution was cooled to 23° C. The crystal was separated and dried under reduced pressure only to recover 11.60 g (76.9%) of a recrystallized product. The compositions of the crude lactide and the recrystallized product as analyzed in the same manner as in Example 10 were as follows.

|  | Crude Lactide (%) | Recrystallized Product (%) |
|---|---|---|
| L-Lactide | 85.0% | 93.9% |
| Meso-lactide | 4.6% | 0.5% |
| Lactic acid monomer | 5.9% | 0.1% |
| Lactic acid dimer | 1.4% | 0.0% |
| Lactic acid trimer | 0.6% | 0.1% |

As described and demonstrated above, the present invention provides a process for producing lactides with an optical purity suited for production of biodegradable polymers. The optical purity of lactides can be arbitrarily selected by controlling the production ratio of a meso-compound by controlling the kind and the amount of a catalyst. The present invention also provides a process for purifying a lactide in a high yield.

While the invention has been described in detail and with reference to specific examples thereof, it will be apparent to one skilled in the art that various changes and modifications can be made therein without departing from the spirit and scope thereof.

What is claimed is:

1. A process for purifying a crude lactide comprising recrystallizing a crude lactide using (A) a poor solvent in which said lactide has a solubility of not more than 1% by weight at 23° C. and (B) a good solvent in which said lactide has a solubility of not less than 5% by weight at 23° C., wherein said good solvent has a boiling point of at least 50° C.

2. A process for purifying a crude lactide as claimed in claim 1, wherein said good solvent (B) is at least one solvent selected from the group consisting of aliphatic tertiary alcohols, ketones, and esters.

3. A process for purifying a crude lactide as claimed in claim 1, wherein said poor solvent (A) is an aliphatic hydrocarbon having from 5 to 12 carbon atoms and said good solvent (B) is an aliphatic tertiary alcohol.

4. A process for purifying a crude lactide comprising recrystallizing a crude lactide using an aliphatic tertiary alcohol and further recrystallizing the product using (C) an aromatic hydrocarbon solvent and (D) an aliphatic hydrocarbon solvent having from 5 to 12 carbon atoms.

5. A process for purifying a crude lactide as claimed in claim 1, comprising further recrystallizing the recrystallization product using (C) an aromatic hydrocarbon solvent and (D) an aliphatic hydrocarbon solvent having from 5 to 12 carbon atoms.

* * * * *